US009145349B2

(12) United States Patent
Dubois

(10) Patent No.: US 9,145,349 B2
(45) Date of Patent: Sep. 29, 2015

(54) METHOD FOR PRODUCING DIALKOXY ALKANES BY PARTIAL OXIDATION OF LOWER ALCOHOLS IN THE PRESENCE OF A CATALYST BASED ON MOLYBDENUM AND IRON

(71) Applicant: Arkema France, Colombes (FR)

(72) Inventor: Jean-Luc Dubois, Millery (FR)

(73) Assignee: ARKEMA FRANCE, Colombes (FR)

( * ) Notice: Subject to any disclaimer, the term of this patent is extended or adjusted under 35 U.S.C. 154(b) by 164 days.

(21) Appl. No.: 14/059,608

(22) Filed: Oct. 22, 2013

(65) Prior Publication Data

US 2014/0066660 A1    Mar. 6, 2014

Related U.S. Application Data

(63) Continuation of application No. 13/003,077, filed as application No. PCT/FR2009/051456 on Jul. 21, 2009, now abandoned.

(30) Foreign Application Priority Data

Jul. 22, 2008   (FR) ...................... 08 54966

(51) Int. Cl.
   *C07C 41/50*   (2006.01)

(52) U.S. Cl.
   CPC ..................... *C07C 41/50* (2013.01)

(58) Field of Classification Search
   None
   See application file for complete search history.

(56) References Cited

U.S. PATENT DOCUMENTS

| 2,663,742 A | 12/1953 | Frevel et al. |
| 6,037,290 A | 3/2000 | Wachs et al. |
| 6,403,841 B1 | 6/2002 | Iwasawa et al. |
| 7,468,341 B2 | 12/2008 | Conca et al. |
| 7,759,525 B2 | 7/2010 | Dubois et al. |
| 2005/0059839 A1 | 3/2005 | Liu et al. |
| 2005/0154226 A1 | 7/2005 | Liu et al. |

FOREIGN PATENT DOCUMENTS

WO    WO2007/128941    11/2007

OTHER PUBLICATIONS

Edwards (Journal of Catalysis, vol. 50, Issue 1, Oct. 1977, pp. 24-34).

Deshmukh et al. , Applied Catalysis A: General, vol. 289, Jun. 2005, pp. 240-255.
Le Page, J-F., et al., "Catalyse de contact", Editions Technip, (1978), pp. 385-393.
Twigg, M., "Catalyst Handbook", Wolfe Publishing Ltd, (1989), pp. 490-503.
Pernicone, N. et al., On the Mechanism of CH3OH Oxidation to CH2O over MoO3-Fe2(MoO4)3 Catalyst, Journalof Catalysis 14, (1969), pp. 293-302.
Liu, H. et al., "Selective Oxidation of Methanol and Ethanol on Supported Ruthenium Oxide Clusters at Low Temperatures", J. Phys. Chem. B, (2005), pp. 2155-2163.
Yuan, Y., et al., "The new catalytic property of supported rhenium oxides for selective oxidation of methanol to methylal", ChemComm, (2000), pp. 1421-1422.
Yuan, Y. et al., "Performance and Characterization of Supported Rhenium Oxide Catalysts for Selective Oxidation of Methanol to Methylal", J. Phys. Chem. B, (2002), pp. 4441-4449.
Yuan,Y., et al., "Selective Synthesis of Methylal from Methanol on a New Crystalline SbRe2O6 Catalyts", Chemistry Letters, (2000), pp. 674-675.
Yuan, Y., et al., "Performance and Characterization of a New Crystalline SbRe2O6 Catalyts for Selective Oxidation of Methanol to Methylal", Journal of Catalysis 195, (2000), pp. 51-61.
Liu, H., et al., "Selective One-Step Synthesis of Dimethoxymethane via Methanol or Dimethy Ether Oxidation on H3+nVnM012−nPO40 Keggin Structures", J. Phys. Chem. B, (2003), pp. 10840-10847.
Fournier, M. et al, "Evidence of B-MoO3Formation during Thermal Treatment of Silica-supported 12-Molybdonhosphoric Acids Catalysts", J Chem. Soc., Chem. Commun., (1994), pp. 307-308.
Tatibouet, J-M., et al. "Catalytic Oxidation of Methanol by 12-Molybdosilicic Acid Supported on Silica: Dispersion Effect", J. Chem. Soc. Chem Commun., (1988), pp. 1260-1261.
Sambeth, J. et al. "Study of the Adsorption/ Oxidation of Methanol over Vanadium Pentoxide", Science Technology, (1995), pp. 171-180.
Twigg, M., et al., "Catalyst Handbook", Wolfe Publishing Ltd, (1989), pp. 489-499.
Le Page, J-F., et al., "Catalyse de contact", Editions Technip, (1978), pp. 400-401.
Zabetakis, M., et al., "Flammability Characteristics of Combustible Gases and Vapors", Bureau of Mines, (1965), pp. 66-68.
Technical Report ISA-TR12.13.01-1999, "Flammability Characteristics of Combustible Gases and Vapors", Figures 75, 76 and Table 13.

*Primary Examiner* — Rosalynd Keys
(74) *Attorney, Agent, or Firm* — Smith, Gambrell & Russell, LLP

(57) ABSTRACT

Disclosed herein is a method for producing alkoxy alkanes by direct partial oxidation of a lower alcohol with a catalyst based upon mixed oxide containing molybdenum and at least one other metal selected from the metals that can assume a trivalent oxidation state such as Fe, Bi, Al, Cr, In, La, Sb, and/or a metal selected from Ni, Co, Cu, V, W, Ti, Ta, Nb, Mn, Sn, P.

17 Claims, 1 Drawing Sheet

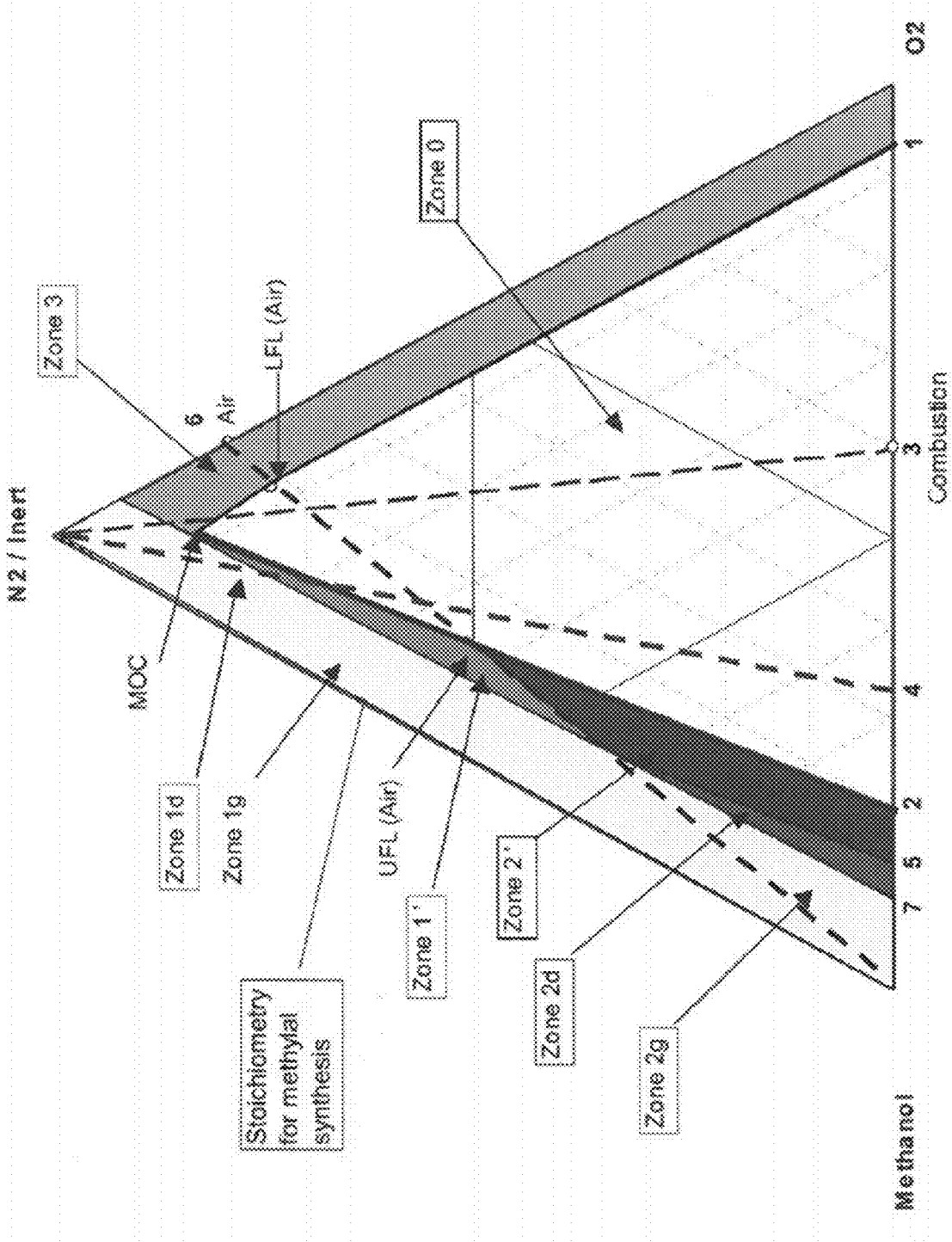

METHOD FOR PRODUCING DIALKOXY ALKANES BY PARTIAL OXIDATION OF LOWER ALCOHOLS IN THE PRESENCE OF A CATALYST BASED ON MOLYBDENUM AND IRON

The present invention relates to a method of producing dialkoxyalkanes by direct partial oxidation of a light alcohol with a catalyst based on a mixed oxide containing molybdenum and iron.

The dialkoxyalkanes from the method of the invention correspond to the following general formula:

RR'CH—O—CRR'—O—CHRR' in which R and R' are either H, or a $CH_3$—$(CH_2)_n$— radical, n being between 0 and 2, such that the total number of carbon atoms of the R and R' radicals is ≤3.

These compounds are obtained by oxidation of light alcohols, that is to say linear alcohols comprising from 1 to 4 carbon atoms. These are primary alcohols such as methanol, ethanol, 1-propanol, 1-butanol or secondary alcohols such as 2-propanol (or isopropanol) or 2-butanol.

When the synthesis reaction is carried out with primary alcohols, the general formula of the dialkoxyalkanes is simplified: $RCH_2$—O—CHR—O—$CH_2R$. This is the formula of the most industrially sought-after dialkoxyalkanes, namely dimethoxymethane (or methylal) and 1,1-diethoxyethane (or acetal).

The methods for oxidation of alcohols and especially light monoalcohols have been well known for at least one century. This oxidation can take two routes distinguished by the reaction mechanism used. The first route is "simple" oxidation, which will be the subject of the developments herein below, and the second route is that of dehydrogenation.

This second route can be carried out in the form of nonoxidizing dehydrogenation according to the following reaction mechanism:

$RCH_2OH \rightarrow RCHO+H_2$ with, therefore, production of hydrogen (with a deficit of oxygen), or in the form of oxidizing dehydrogenation (oxydehydrogenation) and with production of water by oxidation of the hydrogen. These reactions are carried out in the gas phase in the presence, for example, of a reduced copper catalyst or a metallic silver catalyst at temperatures generally between 600 and 700° C. Reference may be made, on this subject, to works such as that of the Institut Français du Pétrole [French Institute of Oil], "Catalyse de Contact" [Contact Catalysis] published by Editions Technip (1978) pages 385-393 or the Catalyst Handbook by M. V. Twigg published by Wolfe Publishing Ltd (1989) pages 490 to 503. These methods are generally used to synthesize aldehydes (formol from methanol) or acids or esters.

As regards the first route of simple oxidation with oxygen, it is well known that the oxidation of methanol in the presence of catalysts results, at low temperature, in the production of a mixture of various oxidized compounds such as, in particular, formaldehyde, methyl formate or methylal (dimethoxymethane).

The various catalytic reactions then brought into play with methanol may be illustrated by the following scheme:

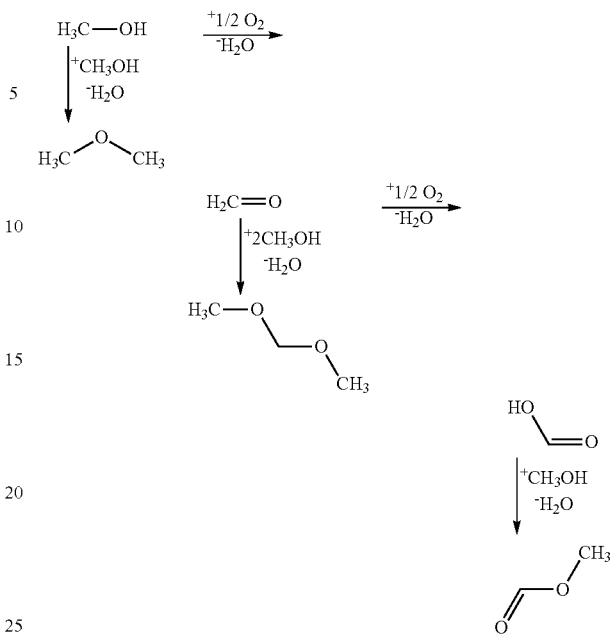

The same scheme may be transposed to ethanol and to other light alcohols.

The conventional methods that target the production of the aldehyde by a partial oxidation of the alcohol thus correspond to the following reaction, in the case of primary alcohols:

$2RCH_2OH+O_2 \rightarrow 2RCHO+2H_2O$

The methods for complete oxidation of the light alcohols make it possible to synthesize acids (then the corresponding esters) according to the following overall reaction:

$2RCH_2OH+2O_2 \rightarrow 2RCOOH+2H_2O$ which is the result of the following two steps:

$2RCH_2OH+O_2 \rightarrow 2RCHO+2H_2O$ $2RCHO+O_2 \rightarrow 2RCOOH,$ followed by the esterification:

$2RCOOH+2RCH_2OH \rightarrow 2RCOOCH_2R+2H_2O$

Unlike the methods of the second route, the methods of partial oxidation of light alcohols also make it possible to form dialkoxyalkanes according to the following overall reaction that corresponds to primary alcohols:

$6RCH_2OH+O_2 \rightarrow 2RCH_2ORCHOCH_2R+4H_2O$ which is the result of two successive steps:

$2RCH_2OH+O_2 \rightarrow 2RCHO+2H_2O$ $2RCHO+4RCH_2OH \rightarrow 2RCH_2ORCHOCH_2R+2H_2O$ It is common practice to distinguish between, on the one hand, total or deep oxidations which make it possible to form acids or esters, and partial oxidations which stop at the aldehyde or dialkoxyalkane stage.

The concomitance of these various reactions and the presence of the various molecules in the medium are illustrated, for example, by the articles by N. Pernicone et al. in "On the Mechanism of $CH_3OH$ Oxidation to $CH_2O$ over $MoO_3$—$Fe_2(MoO_4)_3$ Catalyst" published in Journal of Catalysis 14, 293-302 (1969) and by Haichao Liu and Enrique Iglesia published in J. Phys. Chem. B (2005), 109, 2155-2163 "Selective Oxidation of Methanol and Ethanol on Supported Ruthenium Oxide Clusters at Low Temperatures".

Similar mechanisms are used in the oxidation reactions of secondary light alcohols such as 2-propanol and 2-butanol.

The initial oxidation of the alcohol leads to a ketone of formula $CH_3$—CO—$CH_3$ with isopropanol and $CH_3$—CO—$C_2H_5$ with 2-butanol. The following reaction step of the ketone with the light alcohol leads to dialkoxyalkanes of respective formulae $(CH_3)_2CH$—O—$C(CH_3)_2$—O—CH $(CH_3)_2$ and $(C_2H_5)(CH_3)CH$—O—$C(CH_3)(C_2H_5)$—O—CH $(CH_3)(C_2H_5)$. The overall reaction for the oxidation to the dialkoxyalkane 2,2-diisopropoxypropane from isopropanol is summarized as follows.

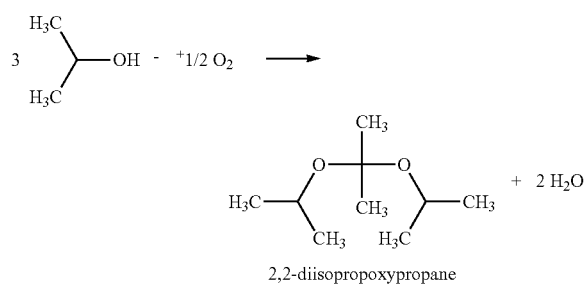

2,2-diisopropoxypropane

Research studies having an industrial objective have therefore turned towards the study of the operating conditions, temperature, liquid phase or gas phase and especially catalysts for the method that makes it possible to obtain the "target" oxidized compound, aldehyde, acid and/or ester or dialkoxyalkane. The problem to be solved is to obtain, by direct oxidation of the charge of alcohol, the desired "target" product with, simultaneously, a high conversion and a high selectivity.

The conventional industrial methods for producing the aldehyde by conventional oxidation (first route) correspond to the following reaction:

$$2RCH_2OH+O_2 \rightarrow 2RCHO+2H_2O$$

This oxidation is carried out in the gas phase in the presence of mixed oxide type catalysts at a temperature between 200 and 400° C. In the latter case, the oxygen present within the reaction medium is in excess but used in dilute form, the substantially equal partial pressures of $O_2$ and alcohol are around a few %, therefore having an $O_2$/alcohol molar ratio>1, the main part of the reaction medium being composed of inert compounds in order not to be under flammable conditions. The use of a large stoichiometric excess of oxygen at a relatively high temperature may result, if precautions are not taken, in complete oxidation and therefore in the homologous acid of the alcohol (see the preceding scheme) by oxidation of the aldehyde, the reaction furthermore possibly continuing even further to result in the "combustion" of the acid, producing carbon dioxide and water.

The manufacture of formol or formaldehyde was, and still is, a particularly attractive sector, which explains the abundance of literature on this subject, whereas the basic methods date back to the start of the last century for the dehydration route and to 1931 for the oxidation route.

The aforementioned article by N. Pernicone et al. refers to a method for the industrial synthesis of formaldehyde, the Montedison process, catalysed by a mixed oxide based on molybdenum and iron and cites a study on the reaction mechanism of this type of reaction, including parasitic secondary reactions.

Mention may also be made of U.S. Pat. No. 7,468,341 which describes a catalyst for oxidation of methanol to formaldehyde consisting of a mixed Fe—Mo oxide associated with a mixed oxide containing cerium or alternatively Application WO 99/52630 which, in a method for oxidation of methanol to formaldehyde, is targeted at the in situ regeneration of the iron molybdate catalyst. All of the above illustrates the essential role that this type of catalyst plays on the industrial scale in the manufacture of formaldehyde.

The studies carried out for the synthesis of specific (target) oxidation compounds of alcohols have mainly related to the study of the types of catalysts suitable for the implementation of such a specific oxidation. Note may be taken, regarding the conventional synthesis of aldehydes, of the following studies:

For the complete oxidation resulting in formic acid or its ester, methyl formate, Patent Application US 2005/0059839 A1 may be cited which describes catalysts for the oxidation of methanol composed of platinum-group metals (ruthenium) deposited on a support. This patent application corresponds to the studies by H. Liu and E. Iglesia targeted in the abovementioned publication.

Specific studies have been carried out on the methods for partial oxidation of alcohols, for the synthesis of methylal, and relating, in particular, to the catalysts to be used in this type of method.

Mention may be made of the following documents.

U.S. Pat. No. 2,663,742 describes a method of producing methylal by oxidation in the vapour phase of methanol in the presence of a catalyst and a halogen or a hydrogen halide.

Several studies have focused on the use of rhenium-based catalysts. U.S. Pat. No. 6,403,841 describes a process for producing methylal by oxidation of methanol over a rhenium-antimony-based catalyst ($SbRe_2O_6$). The reaction is carried out with an excess of oxygen in the presence of a large volume of inert gas (by volume: 5% methanol, 10% oxygen and 85% helium, $O_2$/methanol ratio=2). These studies carried out by Y. Yuan, et al. have been the subject of several publications such as *Chem. Comm.*, 2000, 1421-1422, which describes catalysts based on supported or unsupported rhenium and also in: *J. Phys. Chem. B*, 2002, 106, 4441; *Topics in Catalysis*, vol 22, No 1/2, January 2003; *Chemistry Letters* 2000, 674 and *J. Catal.* 195 (2000) 51-61.

Other studies have been carried out on the use of molybdenum-based catalysts.

US Application No. 2005/0154226 A1 describes a method for producing methylal by oxidation of methanol and/or dimethyl ether. The reaction is carried out over a heteropolyacid catalyst of formula $H_{3+n}XV_nMo_{12-n}O_{40}$, where X represents phosphorus or silicon, and n a value of 0 to 4. The best results seem to be obtained with a $H_5PV_2Mo_{10}O_{40}$ catalyst on silica. These studies have also been published in *J. Phys. Chem. B* 2003, 107, 10840-10847. M. Fournier, C. Rocchicciolo-Deltcheff, et al. describe the evaluation of catalysts of formula $H_3PMo_{12}O_{40}$/silica for the oxidation of methanol to methylal (*J. Chem. Soc., Chem. Commun.* 1994, 307-308). The same team describes the use, in the same reaction, of a catalyst of formula $H_4SiMo_{12}O_{40}$/silica (*J. Chem. Soc., Chem. Commun.* 1998, 1260-1261).

The Applicant has filed a Patent Application WO 2007/034264 describing the use, in this type of method for partial oxidation of a light alcohol, of a catalyst composed of a mixed oxide based on molybdenum and vanadium combined, where appropriate, with other metal elements. The preferred catalyst corresponds to the formula $Mo_{12}V_3W_{1.2}Cu_{1.2}Sb_{0.5}O_x$, x being a numerical value determined by the degree of oxidation of the other elements. This type of catalyst makes it possible in particular to obtain high yields of acetals over a wide range of methanol partial pressures and over a wide range of $O_2$/methanol ratio.

Furthermore, the Applicant has also filed a Patent Application WO2007/128941 which describes a catalytic method for partial oxidation of a light alcohol employing a light alkane as inert gas for diluting the reaction medium. This type of method can be used for the synthesis of methylal with the catalyst of Patent Application WO2007/034264.

Furthermore, J. Sambeth, L. Gambaro and H. Thomas, *Adsorption Science Technology* (1995) page 171, use vanadium pentoxide for the oxidation of methanol, the methylal being one of the products derived from the reaction.

None of the catalysts known for the preparation of a partial oxidation product of a light alcohol in the form of a dialkoxyalkane such as, for example, methylal by direct oxidation of methanol gives complete satisfaction. The object of the present invention is to overcome these drawbacks and to provide a method for the synthesis of a dialkoxyalkane by direct partial oxidation of a light alcohol that makes it possible to attain, simultaneously, yields, productivities and selectivities that are high in dialkoxyalkane.

The subject of the present invention is therefore a method for producing a partial oxidation product of a light alcohol, in the form of a dialkoxyalkane, in which a light alcohol comprising from 1 to 4 carbon atoms is subjected to oxidation by contact in the gas phase with oxygen or a gas containing molecular oxygen in the presence of a catalyst corresponding to the following composition:

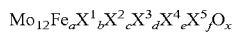

in which Mo=molybdenum; O=oxygen; Fe=iron; $X^1$=at least one element chosen from chromium, nickel, cobalt, manganese, tin and copper; $X^2$=at least one element chosen from bismuth, antimony, tellurium, indium, aluminium and silicon, $X^3$=at least one element chosen from phosphorus, tungsten, titanium, vanadium, tantalum and niobium; $X^4$=at least one element chosen from alkaline-earth metals, lanthanum and cerium; $X^5$ is at least one element chosen from alkali metals; and a, b, c, d and e are indices whose values are $1.5 \leq a \leq 8$; $0 \leq b \leq 4$; $0 \leq c \leq 5$; $0 \leq d \leq 2$; $0 \leq e \leq 2$; $0 \leq f \leq 2$ and x is a numerical value determined by the degree of oxidation of the other elements, and characterized in that, within the reaction medium, the partial pressure of alcohol is between 15 and 80% and preferably between 20 and 50% and that of oxygen is between 2 and 20%, the ratio of the $O_2$/alcohol partial pressures being less than or equal to 1 and preferably between 0.5/6 and 1, the remainder of the medium being composed of a gas that is inert towards the reaction.

A light alcohol in the method of the present invention denotes a linear alcohol having 1 to 4 carbon atoms, in other words methanol, ethanol, propanol and butanol, the alcohol functional group being placed at position 1 or 2 for the latter two.

In the catalyst, the Mo/Fe atomic ratio will be between 1.5 and 8 and preferably between 2.5 and 4.5 to give the industrial catalyst a better service life and better stability.

In the method of the invention, use will be made of mixed oxides of molybdenum and iron which could be associated with at least one metal capable of adopting the degree of oxidation, three, such as bismuth, aluminium, chromium, indium, antimony and tellurium, and/or at least one metal chosen from phosphorus, tungsten, vanadium, nickel, cobalt, copper, titanium, tantalum, niobium, manganese, tin and silicon which in general plays more the role of a binder than a component of the active phase of the catalyst.

The preferred catalysts of the method of the invention will be those which will combine, in the form of mixed oxides, molybdenum and iron or molybdenum, iron and bismuth. Mention may be made, for example, of the mixed oxides of formulae: $MoO_3$—$Fe_2(MoO_4)_3$, $Mo_{12}BiFe_{3.7}Co_{4.7}Ni_{2.6}K_{0.09}Sb_1Si_{7.9}O_x$ or $Mo_{12}BiFe_{3.7}Co_{4.7}Ni_{2.6}K_{0.09}Ti_{0.5}Si_{19}O_x$.

In order to carry out the oxidation of the light alcohol, a gaseous starting charge composed of a mixture of the gaseous light alcohol to be oxidized, molecular oxygen or a gas containing molecular oxygen, such as air, and also, optionally, a diluent gas (other than nitrogen from the air) is introduced into the reactor containing the catalyst. In order to arrive at the composition ranges defined above, use will preferably be made of diluted air or an alcohol/air mixture while ensuring the presence of an excess of oxygen relative to the stoichiometry of the reaction in order to prevent degradation of the catalyst.

The gaseous charge will be composed of a mixture of a light alcohol and oxygen generally in the presence of an inert gas, usually nitrogen from the air, having a high alcohol content such that the partial pressure of alcohol within the reaction medium is greater than 15 and less than or equal to 80% and preferably between 20 and 50% and that of oxygen is between 2 and 20%.

The concentration of the light alcohol in the gas stream, expressed as a partial pressure, is advantageously between 25 and 40%, preferably between 30 and 37%. Use will preferably be made of a mixture of air and the alcohol to be oxidized, in order to simplify and optimize the operating conditions while avoiding as much as possible the recycling of the co-products $CO$, $CO_2$, $N_2$ of the reaction.

The molar ratio of oxygen (calculated as $O_2$) to the light alcohol is below 1 and preferably between 0.5/6 and 1/1. The choice of the respective amounts of oxygen and of alcohol depends on the type of implementation of the method, either seeking a complete conversion, in which case it is necessary to be above the stoichiometry of the reaction, or a partial conversion for which a deficit of oxygen with respect to the stoichiometry suffices. Use will preferably be made of a ratio of 1.2/6 to 0.9/1. The gas containing molecular oxygen may be air or oxygen-enriched air. Preferably, air is used as a mixture with the alcohol to be oxidized.

The reaction carried out in the gas phase will generally be carried out at a temperature between 10 and 400° C. and under a pressure between 50 and 1000 kPa and with a space velocity for introducing the reaction mixture between, in particular, 2000 and 100 000 $h^{-1}$.

The oxidation is carried out by contact in the vapour phase at a temperature in particular of 10 to 400° C., preferably from 100 to 350° C., and more preferably from 200 to 300° C.

The oxidation is carried out by contact in the vapour phase at a pressure generally between 50 and 1000 kPa, preferably between 100 and 500 kPa.

The space velocity for introducing the reaction mixture is generally between 2000 and 100 000 $h^{-1}$, preferably between 11 000 and 44 000 $h^{-1}$.

The preferred dialkoxyalkanes which may be obtained according to the method of the invention are dimethoxymethane, also known as methylal or formaldehyde dimethyl acetal, and 1,1-diethoxyethane or acetal. The present invention relates more particularly to the preparation of these two alkoxyalkanes and especially of methylal by direct (in one step) partial oxidation starting from methanol (or ethanol) and oxygen or a gas containing oxygen, the stoichiometry of the overall reaction being the following:

This reaction, applied to the oxidation of ethanol to obtain acetal or 1,1-diethoxyethane, corresponds to:

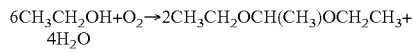

This is because the Applicant has surprisingly discovered that catalysts based on a mixed oxide of molybdenum and iron, widely used for the synthesis of formaldehyde starting from methanol, make it possible to obtain, by direct oxidation of the methanol, high yields (conversion and selectivity) of methylal and that they also make it possible to synthesize 1,1-diethoxyethane from ethanol. This is because the Applicant has surprisingly observed, regarding catalysts dedicated to aldehyde synthesis, that high yields of acetals could be obtained by using, in the presence of catalysts such as defined in the general formula defined above, an air/alcohol mixture with a high alcohol content greater than 15%, preferably containing from 30 to 40% alcohol. For example, use will be made of an air/alcohol mixture having 35% alcohol, or a ternary $O_2/N_2$/alcohol mixture having a composition close to 13/52/35 and therefore an $O_2$/alcohol ratio of 13/35.

Compared to the prior art, the advantages, apart from the performance as regards yield and selectivity, are a greater productivity and a lower consumption of energy since it is not necessary to use a high flow rate or high concentration of diluent inert gas to keep the reaction mixture outside of the flammability zone of the alcohol/oxygen/inert gas mixture. In the case of the use of inert gas(es) in sufficient amount(s) to remain outside of the flammability limits, these will advantageously be chosen from: nitrogen, $CO_2$, $H_2O$ and $CH_4$. It will be carried out in the absence of halogens or hydrogen halides in order to prevent the formation of halomethanes.

It may be noted that these conditions are highly different from those described in U.S. Pat. No. 2,663,742, where the MeOH/$O_2$ molar ratio is greater than 12, but where the reaction is carried out in the presence of chlorine. The conditions of the present reaction are, in particular, an MeOH/$O_2$ molar ratio below 12 and preferably below 6, since it is desired, on the one hand, to be outside of the flammability zone and, on the other hand, to have enough $O_2$ at the outlet of the reactor to maintain the stability of the catalyst when working at a high conversion.

The method may be carried out in any reactor technology using a solid catalyst which makes it possible to effectively eliminate the heat of reaction. Mention may be made, for example, of multitubular fixed beds, circulating fluidized beds, or else fluidized beds. The catalyst is then shaped according to the chosen reactor technology, by techniques well known to persons skilled in the art; for example, in the form of pellets, rings (hollow cylinders), solid extrudates or else catalysts supported on an inert material, for example beads of steatite, of alumina, of silica, of silica-alumina or of silicon carbide in the case of a fixed bed. In the case of a fluidized bed or a circulating fluidized bed, the catalyst may be shaped, for example, by spraying in the presence of a binder such as silica in order to give it the necessary mechanical strength.

Preferably, a reactor with a fixed bed containing the catalyst will be used.

It is then advantageously possible to carry out the oxidation of methanol (or ethanol or another light alcohol) in a fixed-bed oxidation reactor containing the catalyst in order to obtain an effluent that is subjected to a separation step. Obtained in this step is, on the one hand, at the top, an effluent of light gases comprising, where appropriate, the diluent gas or gases, CO, $CO_2$, nitrogen from the air ($N_2$) when air has been used as the gas containing molecular oxygen, and residual $O_2$ and, on the other hand, at the bottom, the effluent of methylal (acetal or dialkoxyalkane) and water which is subjected to a distillation step to separate the desired dialkoxyalkane at the top and water at the bottom. At least one part of said effluent of light gases may be used in the boiler.

It is possible to use molecular oxygen or oxygen-enriched air as an oxidant and methane as an additional diluent; an effluent of light gases comprising $CH_4$, CO, $CO_2$, $N_2$ and residual $O_2$ is then obtained which can, where appropriate, be recycled to the inlet of the oxidation reactor and/or be subjected to a purification step in order to separate a CO and/or $CO_2$ and/or $O_2$ effluent before recycling it to the inlet of the oxidation reactor.

As has been indicated several times, all these methods for oxidation of alcohols, and therefore of fuels, may be carried out according to the choice of compositions of the ternary mixture under flammability conditions of the alcohol/oxygen mixture. These conditions are not an obstacle that nullifies an industrial exploitation but they require operating precautions which, due to their cost, must be avoided as much as possible. It is therefore preferable to operate under strict safety conditions, that is to say by being sure not to work in the flammability zone of the alcohol/oxygen mixture.

In order to do this, it is possible to refer to certain determinations of this zone in various cases taking into account the components of the mixture, the operating temperature and the pressure. The diagram from FIG. 1 illustrates this flammability zone for a ternary methanol/oxygen/inert gas mixture at a temperature of 25° C. and at atmospheric pressure.

To determine the optimal reaction conditions outside of the flammability zone, reference could be made to various publications on the subject. Apart from the aforementioned "Catalyst Handbook" page 498 and the work "Catalyse de Contact" [Contact Catalysis] page 400, mention may be made of the article by Michael G. Zabetakis "Flammability Characteristics of Combustible Gases and Vapors", Bureau of Mines Bulletin 627, pages 66 to 68 and the Technical report ISA-TR12.13.01-1999 "Flammability Characteristics of Combustible Gases and Vapors" FIGS. 75 and 76 and Table 13.

The appended FIG. 1 is presented to better illustrate the operability conditions, outside of the flammability zones, of the method that is the subject of the present invention under standard temperature and pressure conditions, 25° C. and 1 atm.

In FIG. 1, the bold lines 1 and 2 specify the contents that are respectively the lower (1) and upper (2) flammability limits. They define, with the methanol-$O_2$ axis, the flammability zone of the mixture which substantially takes the shape of a triangle (Zone 0), the apex of which is the maximum oxygen content (MOC). The points denoted by LFL (Air) and UFL (Air) correspond to these lower and upper limits in the case of using air as an oxidant. Between these lines (1) and (2) the mixture is in the flammable Zone 0. The parts located above these lines illustrate non-flammable mixtures. The right-hand part, Zone 3, is that where the concentration of alcohol is low and that of oxygen is larger or smaller but always below the flammability threshold, whereas, in the left-hand part, Zones 1 and 2 correspond to a low oxygen content (above the flammability threshold). Lines 3, 4 and 5 correspond to the stoichiometries of the main oxidation reactions of the alcohol, in this case methanol; a transposition to ethanol could be easily carried out using the appropriate flammability diagram. Line 3 corresponds to the combustion of methanol ($CH_3OH + 3/2\ O_2 \rightarrow CO_2 + 2\ H_2O$), line 4 to the oxidation to formol ($CH_3OH + \frac{1}{2}\ O_2 \rightarrow CH_2O + H_2O$), line 5 to the synthesis of methylal ($3\ CH_3OH + \frac{1}{2}\ O_2 \rightarrow CH_3OCH_2OCH_3 + H_2O$) and finally line 6 to air, that is to say the straight line joining the methanol apex to the $80/20\ N_2$ (inert)/$O_2$ mixture.

Zone 1 corresponds to mixtures in which an oxygen content below that of air is used (use of diluted air). It is located entirely above line 6.

Zone 2 corresponds to mixtures in which an oxygen content greater than that of air is used. It is located entirely below line 6.

Inside these two zones it is possible to provide some information specific to the methylal formation reaction (line 5). Specifically, if the straight line parallel to the left-hand axis is plotted passing through the apex of the flammable zone (Zone 0): line 7, zone 1 is delimited into two parts 1d and 1g on the one hand and 1' on the other hand. In the Zone 1d/1g, the oxygen content is still below the MOC and there is the guarantee of therefore being outside of the flammability zone. In zone 1', there is more oxygen than the MOC, but while still being outside of the flammability zone. On either side of line 5 there are Zones 1g and 1d. In Zone 1g, there is less oxygen than the stoichiometry, which mathematically will not make it possible to have 100% yield of methylal. In zone 1d, there is more oxygen than the stoichiometry for the synthesis of methylal; it is therefore possible to hope for high conversions and yields. It is possible in each of Zones 1 and 2 to distinguish zones: 1d, 1g and 1' and 2d, 2g and 2'.

In Zones 1, the reaction may be carried out with air as an oxidant.

In Zones 2d, 2g and 2', the reaction should be carried out with an addition of molecular oxygen. Zone 3 is the zone delimited by the lower flammability limit.

Zones 1d, 1g and 2g are delimited by the maximum oxygen content (MOC). Below this oxygen content, there is the guarantee of being outside of the flammability limits. It is therefore preferred to work in this zone for safety reasons.

Zones 1', 1d and 1g and 2g, 2d and 2' are delimited by the stoichiometry line for the methanol→methylal reaction ($6\ CH_3OH/O_2$). To the right of this line, there is enough oxygen to have a complete conversion of methanol to 100% selectivity of methylal; on the left, there is not enough oxygen and the conversion will only be partial. It is therefore preferred to work in the zones 1', 1d and 2'.

In the method of the invention, the preferred zones are Zones 1d, 1' and 1g in which it is possible to work with high contents both of alcohols (30 to 40% or even 50 or 60% by volume) and of oxygen, of around 15%, while still working with air as a source of oxygen and being free from using a large source of inert gas. It should be noted that the maximum content of $O_2$ depends on the alcohol and it rises with the number of carbons of the alcohol.

It is preferred to use an oxidant gas that is rich in air in order to reduce electricity consumption at the gas compressors. In this configuration, it is not necessary to recycle oxygen-depleted gases of the reaction in order to dilute the oxygen from the air of reaction and therefore the method is simplified.

This ternary diagram may be transposed, on the one hand, with the same constituents under different temperature and pressure conditions and, on the other hand, to other alcohols, referring to the publications cited above and especially that of Zebetakis. Represented on page 67 of this publication is a table from which it is possible to deduce the maximum oxygen contents according to the alcohol used.

Methylal finds many applications in various fields due to its remarkable properties: an exceptional solvating power; its amphiphilic character: methylal is both hydrophilic and lipophilic; a low viscosity; a low surface tension; and a particularly high evaporation rate.

The fields of application for methylal are especially the following: aerosols for cosmetic and technical applications; paints and varnishes with methylal as a solvent; paint strippers; cleaning and degreasing solvents; pharmaceutical products with methylal as a support or as a reagent; in the synthesis of resins; quick-drying adhesives; in the extraction of flavours, aromatic products and fragrances; additives for diesel fuels; insecticides; electrochemical cells, where methylal is a reactant in the production of polyoxymethylene dimethyl ethers used as fuels in fuel cells.

Diethyl acetal or acetaldehyde acetal, also known as 1,1-diethoxyethane, is an important raw material for the perfume industries and pharmaceutical products. Added to perfumes, it increases their resistance to oxidation and consequently their lifetime, whereas it acts as a flavour enhancer in spirits. It also has many applications in the chemical and pharmaceutical industry where it is used as a solvent but also as an intermediate in synthetic chemistry for protecting the carbonyl groups of ketones and aldehydes. Furthermore, it is also a key molecule in the synthesis of various chemical compounds such as alcohol vinyl ethers (used as organic solvents for cellulose and its derivatives, in perfumes and synthetic resins and also in adhesives) or else N-vinylcarboxylic acid amides (raw materials for hydrophilic polymers used in electronic compounds, televisions, motor vehicle equipment and printers).

1,1-diethoxyethane offers many advantages as a fuel additive both in the formulation of petrols and in that of diesel fuels.

It may also be used as an oxygenated additive for diesel fuel since it drastically reduces the emissions of particulates and $NO_x$ whilst it maintains, or even increases, the cetane number and thus facilitates the combustion of the final products without reducing the ignition qualities. It should be noted that a high cetane number indicates the ability of a fuel to ignite after having been injected into the combustion cylinder of a diesel engine. Furthermore, 1,1-diethoxyethane may also be used as an intermediate to form glycerol acetals used in fuels.

The following examples further illustrate the present invention without however limiting the scope thereof.

EXAMPLE 1

Evaluation of the Catalysts

The evaluation of the catalysts was carried out in a fixed-bed reactor. The flow of helium and of oxygen was controlled by mass flow meters. The gas stream passed into an evaporator/saturator containing methanol. The evaporator was either at ambient temperature or heated by heating tapes. The temperature of the saturator was adjusted in order to control the partial pressure of methanol. The temperature of the gas mixture was controlled by a thermocouple at the top of the saturator. The gas mixture was then sent to the reactor which was placed in an oven. The reaction temperature was measured using a thermocouple which was in the catalytic bed.

The gaseous effluents were analysed by in-line gas chromatography using a microGC equipped with 2 columns (molecular sieve and Plot U).

The catalysts were milled and the 250 micron particle size fraction was mixed with a double amount of silicon carbide of the same particle size and placed in the glass reactors.

Calibration of the MicroGC was carried out with reference gas mixtures, and calibration for the condensable products (dimethoxymethane, methanol, methyl formate) was carried out using the evaporator/saturator.

EXAMPLE 2

Oxidation Reaction of Methanol 151 mg of an iron molybdate catalyst MFM3-MS supplied by MAPCO and having an Mo/Fe atomic ratio of 2.5 were mixed with 300 mg of silicon carbide and charged into the reactor. MFM3-MS catalyst: outer diameter=3.9 mm, inner diameter=1.85 mm, height=4.04 mm.

The catalyst was first activated under a helium/oxygen stream (48 Sml/min–12 Sml/min) at 340° C. for 15 hours and 30 minutes. Next, the temperature was brought to 250° C. and the acquisition of data was started. After stabilization, the performance of the catalyst was recorded. Next, the temperature of the catalyst was increased in stages and at each level (260, 271 and 281° C.) data were taken.

The flow rates of oxygen and helium were respectively 6.7 and 26.4 Sml/min and the concentration of methanol was adjusted to 37% (conditions: methanol/$O_2$/inert gas: 37/13/50) for an HSV of 22 000 ml·$h^{-1}$·$g^{-1}$.

The conversion and selectivity results obtained during the catalytic oxidation of methanol are given in Table 1 (DMM=methylal; F=formol; DME=dimethyl ether; MF=methyl formate; CO=carbon monoxide; $CO_2$=carbon dioxide).

TABLE 1

| Catalyst | Temperature (° C.) | Conversion (%) | DMM | F | DME | MF | CO | $CO_2$ | Total |
|---|---|---|---|---|---|---|---|---|---|
| | | | | Selectivities (%) | | | | | |
| MFM3-MS | 250 | 25.3 | 94.3 | 0.1 | 4.9 | 0.6 | — | — | 100 |
| | 260 | 32.3 | 94.3 | 0.3 | 4.9 | 0.6 | — | — | 100 |
| | 271 | 46.5 | 92.7 | 1.3 | 5.2 | 0.7 | 0.1 | — | 100 |
| | 281 | 55.7 | 89.8 | 4.2 | 5.3 | 0.6 | 0.1 | — | 100 |

EXAMPLE 3

Oxidation Reaction of Methanol

The reaction was carried out with a commercial catalyst: ACF-4S (bismuth-iron molybdate type) from Nippon Shokubai. 150 mg of the commercial catalyst cited above were mixed with 300 mg of silicon carbide, then charged into the reactor.

The catalyst was first activated under a helium/oxygen stream (48 Sml/min–12 Sml/min) at 340° C. for 15 hours and 30 minutes. Next, the temperature was brought to 236° C. and the acquisition of data was started. After stabilization, the performance of the catalyst was recorded. Next, the temperature of the catalyst was increased in stages and at each level data were taken.

The flow rates of oxygen and helium were respectively 6.7 and 26.4 Sml/min and the concentration of methanol was adjusted to 37% (conditions: methanol/$O_2$/inert gas=37/13/50 for an HSV of 22 000 ml·$h^{-1}$·$g^{-1}$.

with DMM=methylal; F=formol; DME=dimethyl ether; MF=methyl formate; CO=carbon monoxide; $CO_2$=carbon dioxide.

The conversion and selectivity results obtained are given in Table 2 below:

TABLE 2

| Catalyst | Temperature (° C.) | Conversion (%) | DMM | F | DME | MF | CO | $CO_2$ | Total |
|---|---|---|---|---|---|---|---|---|---|
| | | | | Selectivities (%) | | | | | |
| ACF-4S from Nippon Shokubai "BiMo" | 250 | 6.7 | 88.1 | 5.6 | 5.8 | 0.5 | — | — | 100 |
| | 259 | 9.1 | 87.9 | 5.8 | 5.6 | 0.6 | — | — | 100 |
| | 271 | 13.0 | 88.5 | 5.5 | 5.3 | 0.6 | — | 0.0 | 100 |
| | 280 | 16.7 | 88.3 | 5.9 | 5.1 | 0.7 | — | 0.0 | 100 |

EXAMPLE 4 (COMPARATIVE)

Methanol was oxidized, in accordance with the methods of the prior art, with 150 mg of the commercial catalyst iron molybdate MFM3-MS (MAPCO) which were mixed with 300 mg of silicon carbide, then charged into the reactor.

The catalyst was first activated under a helium/oxygen stream (48 Sml/min–12 Sml/min) at 340° C. for 15 hours and 30 minutes. Next, the temperature was brought to 236° C. and the acquisition of data was started. After stabilization, the performance of the catalyst was recorded. Next, the temperature of the catalyst was increased in stages and at each level (255 and 265° C.) data were taken.

The flow rates of oxygen and helium were respectively 4.7 and 47.6 Sml/min and the concentration of methanol was adjusted to 5% of the reaction medium (Methanol/$O_2$/inert gas: 5/8.5/86.5).

The results are given in Table 3 below.

TABLE 3

| Temperature (° C.) | $CH_3OH$ conversion (%) | DMM selectivity (%) | DMM yield (%) |
|---|---|---|---|
| 236 | 41 | 36 | 15 |
| 255 | 57 | 20 | 11 |
| 265 | 67 | 11 | 7 |

As can be seen by comparison between Tables 1 and 3, the results obtained using a low partial pressure of methanol resulted in much lower dimethoxymethane selectivities and yields than when high partial pressures were used. These results are all the more unexpected since the conversions may be kept at a high level.

EXAMPLE 5

Operating Conditions for the Selective Oxidation of Ethanol

The catalyst was tested in a fixed-bed reactor. The flow rates of the helium and oxygen gases were regulated by a mass flow controller. The gaseous mixture passed through an evaporator/saturator filled with ethanol. The evaporator could be at ambient temperature or heated by a heater cable. The temperature of the saturator was adjusted and controlled in order to obtain the desired partial pressure of ethanol. The temperature was measured using a thermocouple at the outlet of the saturator.

The reaction mixture fed the reactor which was placed in an oven. The temperature of the reaction was measured by a thermocouple placed in the catalytic bed.

The gaseous effluents were analysed in line by a micro-GC equipped with three columns (molecular sieve, Plot U and OV-1).

A stream of helium and oxygen passed through the evaporator/saturator which were adjusted to the appropriate temperatures making it possible to obtain the desired composition of ethanol/oxygen/helium. The catalyst was mixed with a quadruple amount of silicon carbide in the glass reactor.

The calibration of the micro-GC was carried out with reference gas mixtures and the condensable products were calibrated using the evaporator/saturator.

EXAMPLE 6 (COMPARATIVE)

151 mg of the MFM3-MS catalyst (supplied by MAPCO) were mixed with 600 mg of silicon carbide and were charged into the reactor.

The catalyst was activated at a temperature of 340° C. under a helium/oxygen mixture (48 Sml/min/12 Sml/min) for 12 hours. Next, the temperature was decreased to 200° C. and the data were recorded. After stabilization, the efficiency of the catalyst was tested. After acquisition of the data, the temperature of the catalyst was increased to the following temperature: 228° C. then 260° C., where the data were recorded.

The flow rates of oxygen and helium were respectively 12.7 and 51 Sml/min and the temperature of the saturator was adjusted to obtain a molar fraction of ethanol of 2% (ethanol/$O_2$/inert gas=2/19.5/78.5).

The results as regards the conversions and selectivities obtained during the catalytic oxidation of ethanol, expressed as follows: A=acetaldehyde; DEE=1,1-diethoxyethane; EE=ethyl ether; EA=ethyl acetate; AA=acetic acid; E=ethylene; CO=carbon monoxide; $CO_2$=carbon dioxide, are given in Table 4.

TABLE 4

| Temperature (° C.) | Ethanol conversion (%) | A | DEE | EE | EA | AA | E | CO | $CO_2$ |
|---|---|---|---|---|---|---|---|---|---|
| 200 | 31.2 | 92.5 | 6.5 | 1 | — | — | — | — | — |
| 228 | 61.6 | 98.5 | — | 1.5 | — | — | — | — | — |
| 260 | 91.5 | 93.2 | — | 0.9 | 1 | — | 1.9 | 1.4 | 1.6 |

Under these operating conditions, the catalyst was very selective to give acetaldehyde.

EXAMPLE 7

150 mg of the MFM3-MS catalyst (MAPCO) were mixed with 600 mg of silicon carbide and were charged into the reactor.

The catalyst was activated at a temperature of 340° C. under a helium/oxygen mixture (48 Sml/min/12 Sml/min) for 12 hours. Next, the temperature was decreased to 200° C. and the data were recorded. After stabilization, the efficiency of the catalyst was tested. After acquisition of the data, the temperature of the catalyst was increased to the following temperature: 228° C. then 260° C., where the data were recorded.

The flow rates of oxygen and helium were respectively 0.3 and 63.4 Sml/min and the temperature of the saturator was adjusted to obtain a molar fraction of ethanol of 2% to obtain EtOH/$O_2$/inert gas=2/0.5/97.5.

The conversion and selectivity results obtained during the catalytic oxidation of ethanol are given in Table 5.

TABLE 5

| Temperature (° C.) | Ethanol conversion (%) | A | DEE | EE | EA | AA | E | CO | $CO_2$ |
|---|---|---|---|---|---|---|---|---|---|
| 200 | 18.4 | 100 | — | — | — | — | — | — | — |
| 228 | 41.4 | 97.5 | — | 2.5 | — | — | — | — | — |
| 260 | 63.5 | 95.7 | — | 2.1 | — | — | 2.2 | — | — |

Although the catalyst was fed with a stream that was less rich in oxygen than in the case of the preceding example, it remained very selective for the production of acetaldehyde.

EXAMPLE 8

150 mg of the MFM3-MS catalyst (MAPCO) were mixed with 600 mg of silicon carbide and were charged into the reactor.

The catalyst was activated at a temperature of 340° C. under a helium/oxygen mixture (48 Sml/min/12 Sml/min) for 12 hours. Next, the temperature was decreased to 201° C. and the data were recorded. After stabilization, the efficiency of the catalyst was tested. After acquisition of the data, the temperature of the catalyst was increased to the following temperature: 231° C. then 260° C., where the data were recorded.

The flow rates of oxygen and helium were respectively 4.6 and 41 Sml/min and the temperature of the saturator was adjusted to obtain a molar fraction of ethanol of 30% (Ethanol/$O_2$/HE=30/7/63).

The conversion and selectivity results obtained during the catalytic oxidation of ethanol are given in Table 6.

TABLE 6

| Temperature (° C.) | Ethanol conversion (%) | A | DEE | EE | EA | AA | E | CO | $CO_2$ |
|---|---|---|---|---|---|---|---|---|---|
| 201 | 5 | 62 | 36 | 2 | — | — | — | — | — |
| 231 | 10.8 | 68.5 | 28.5 | 3 | — | — | — | — | — |
| 260 | 25.6 | 77.6 | 17.7 | 4.1 | — | — | 0.6 | — | — |

Under these operating conditions, the catalyst produced diethoxyethane which was not detected under the conditions of low partial pressures of ethanol.

EXAMPLE 9

75 mg of the MFM3-MS catalyst (MAPCO) were mixed with 300 mg of silicon carbide and were charged into the reactor.

The catalyst was activated at a temperature of 340° C. under a helium/oxygen mixture (48 Sml/min/12 Sml/min) for 12 hours. Next, the temperature was decreased to 199° C. and the data were recorded. After stabilization, the efficiency of the catalyst was tested. After acquisition of the data, the temperature of the catalyst was increased to the following temperature: 230° C. then 260° C., where the data were recorded.

The flow rates of oxygen and helium were respectively 4.6 and 41 Sml/min and the temperature of the saturator was adjusted to obtain a molar fraction of ethanol of 30% (Ethanol/$O_2$/HE=30/7/63).

The conversion and selectivity results obtained during the catalytic oxidation of ethanol are given in Table 7.

TABLE 7

| Temperature (° C.) | Ethanol conversion (%) | Carbon selectivities (%) | | | | | | |
|---|---|---|---|---|---|---|---|---|
| | | A | DEE | EE | EA | AA | E | CO | $CO_2$ |
| 199 | 2.4 | 26 | 72.7 | 1.3 | — | — | — | — | — |
| 230 | 8.4 | 36.3 | 61.7 | 2 | — | — | — | — | — |
| 260 | 17.2 | 55.9 | 40.4 | 3.3 | — | — | 0.4 | — | — |

Under the conditions of high HSV (short contact time), double that of Example 8, the catalyst proved to be selective for diethoxyethane.

EXAMPLE 10

150 mg of the MFM3-HS catalyst (MAPCO) were mixed with 600 mg of silicon carbide and were charged into the reactor.

MFM3-HS supplied by MAPCO is distinguished from the preceding MFM3-MS in particular by its dimensions but also by its activity: outer diameter=4.35 mm, inner diameter=1.85 mm, height=4.44 mm.

The catalyst was activated at a temperature of 340° C. under a helium/oxygen mixture (48 Sml/min/12 Sml/min) for 12 hours. Next, the temperature was decreased to 198° C. and the data were recorded. After stabilization, the efficiency of the catalyst was tested. After acquisition of the data, the temperature of the catalyst was increased to the following temperature: 230° C. then 260° C., where the data were recorded.

The flow rates of oxygen and helium were respectively 4.6 and 41 Sml/min and the temperature of the saturator was adjusted to obtain a molar fraction of ethanol of 30% (Ethanol/$O_2$/HE=30/7/63). The conversion and selectivity results obtained during the catalytic oxidation of ethanol are given in Table 8.

TABLE 8

| Temperature (° C.) | Ethanol conversion (%) | Carbon selectivities (%) | | | | | | |
|---|---|---|---|---|---|---|---|---|
| | | A | DEE | EE | EA | AA | E | CO | $CO_2$ |
| 198 | 2.4 | 23.8 | 74.7 | 1.5 | — | — | — | — | — |
| 230 | 7 | 37.2 | 60.4 | 2.2 | — | — | 0.2 | — | — |
| 260 | 17.1 | 57.9 | 37.9 | 3.7 | — | — | 0.4 | — | 0.1 |

Here too, the catalyst proved selective for diethoxyethane.

The invention claimed is:

1. A method for selectively producing a partial oxidation product of a light alcohol, in the form of a dialkoxyalkane, comprising
   oxidizing a light alcohol having from 1 to 4 carbon atoms by contact, in the gas phase, with oxygen or a gas containing molecular oxygen in the presence of a catalyst is selected from the group consisting of mixed oxides of formulae: $Mo_{12}BiFe_{3.7}Co_{4.7}Ni_{2.6}K_{0.09}Sb_1Si_{7.9}O_x$, $Mo_{12}BiFe_{3.7}Co_{4.7}Ni_{2.6}K_{0.09}Ti_{0.5}Si_{19}O_x$, and $MoO_3\text{-}Fe_2(MoO_4)_3$; and
   wherein the partial pressure of alcohol is between 15 and 80% and the partial pressure of oxygen is between 2 and 20%, the ratio of the $O_2$/alcohol partial pressures being less than 1, the remainder of the gas phase comprising a gas that is inert towards the reaction.

2. The method according to claim 1, wherein the light alcohol is selected from the group consisting of methanol, ethanol, propanol, isopropanol, n-butanol, and 2-butanol.

3. The method according to claim 1, wherein the molar ratio of oxygen, calculated as $O_2$, to the light alcohol is between 0.5/6 and 1/1.

4. The method according to claim 1, wherein the reaction is carried out at a temperature between 10 and 400° C. and under a pressure between 50 and 1000 kPa and with a space velocity for introducing the reaction mixture between, 2000 and 100 000 $h^{-1}$.

5. The method according to claim 1, wherein the light alcohol is methanol or ethanol and the partial oxidation product is methylal or acetal and the oxidation is carried out by contact in the vapor phase at a temperature of 10 to 400° C., and at a pressure of 50 to 1000 kPa.

6. The method according to claim 5, wherein the concentration of the light alcohol in the gas stream is between 25 and 40%, and that of the oxygen is such that the $O_2$/alcohol ratio is greater than 1.

7. The method according to claim 5, wherein the space velocity for introducing the gaseous mixture is from 2000-100 000 $h^{-1}$.

8. The method according to claim 1, wherein the oxidation of the light alcohol is carried out in a fixed-bed oxidation reactor containing the catalyst.

9. The method according to claim 8, further comprising an effluent is obtained at an outlet of the reactor, and subjecting said effluent to a separation step, to produce a top effluent of light gases comprising the diluent gas or gases, CO, $CO_2$, nitrogen when air has been used as the gas containing molecular oxygen, residual $O_2$, and a bottom effluent of dialkoxyalkane and water and further characterized in subjecting said dialkoxyalkane and water to a distillation to separate the dialkoxyalkane and the water.

10. The method according to claim 1, wherein the partial pressure of alcohol is between 20 and 50%.

11. The method according to claim 1, wherein the ratio of the $O_2$/alcohol partial pressures is between 0.5/6 and 1.

12. The method according to claim 3, wherein the molar ratio of oxygen, calculated as $O_2$, to the light alcohol is between 1.2/6 and 0.9/1.

13. The method according to claim 5, wherein the oxidation is carried out by contact in the vapor phase at a temperature of from 100 to 350° C.

14. The method according to claim 5, wherein the oxidation is carried out by contact in the vapor phase at a temperature of from 200 to 300° C.

15. The method according to claim 5, wherein the oxidation is carried out by contact in the vapor phase at a pressure of from 100 to 500 kPa.

16. The method according to claim 6, wherein the $O_2$/alcohol ratio is between 1.2/6 and 0.9/1.

17. The method according to claim 5, wherein the space velocity for introducing the gaseous mixture is from 11 000-44 000 $h^{-1}$.

\* \* \* \* \*